United States Patent
Kim

(10) Patent No.: US 7,243,527 B2
(45) Date of Patent: Jul. 17, 2007

(54) SENSING APPARATUS FOR A VEHICLE

(75) Inventor: Moo Yong Kim, Suwon (KR)

(73) Assignee: Hyundai Motor Company, Seocho-Ku, Seoul (KR)

( * ) Notice: Subject to any disclaimer, the term of this patent is extended or adjusted under 35 U.S.C. 154(b) by 239 days.

(21) Appl. No.: 11/028,258

(22) Filed: Dec. 30, 2004

(65) Prior Publication Data

US 2006/0000258 A1    Jan. 5, 2006

(30) Foreign Application Priority Data

Jun. 15, 2004    (KR) .................. 10-2004-0044077

(51) Int. Cl.
*G01N 7/00*    (2006.01)
(52) U.S. Cl. .................................................. 73/23.2
(58) Field of Classification Search .................. 73/23.2
See application file for complete search history.

(56) References Cited

U.S. PATENT DOCUMENTS 4,910,463 A * 3/1990 Williams et al. ............ 324/468
7,112,447 B2 * 9/2006 McGee et al. ............... 436/118
2002/0171298 A1 * 11/2002 Chen et al. .................. 307/127
2004/0003664 A1 * 1/2004 Ishikawa et al. ............. 73/644
2004/0145485 A1 * 7/2004 Tice ............................ 340/632

FOREIGN PATENT DOCUMENTS

KR    202000-0019695    11/2000

* cited by examiner

*Primary Examiner*—Michael Cygan
(74) *Attorney, Agent, or Firm*—Morgan Lewis & Bockius LLP

(57) ABSTRACT

The sensing apparatus for a vehicle includes a case having an opening part formed so as to communicate with an outside. A printed circuit board is disposed inside of the case, and includes a circuit unit. A noxious gas sensing part is electrically connected with the circuit unit for sensing a noxious gas of an external air inflowing through the opening portion, and for outputting a sensing signal. A connector is disposed at least partially with the case, one end thereof being directly connected with the circuit unit, and the other end thereof being directly connected with an external device.

7 Claims, 3 Drawing Sheets

SENSING APPARATUS FOR A VEHICLE

CROSS-REFERENCE TO RELATED APPLICATIONS

This application claims priority to Korean Patent Application No. 10-2004-0044077, filed Jun. 15, 2004, the disclosure of which is hereby incorporated by reference.

FIELD OF THE INVENTION

The present invention relates to a sensing apparatus. More particularly, the present invention relates to a sensing apparatus for a vehicle.

BACKGROUND OF THE INVENTION

Generally, a sensing apparatus for a vehicle is to be utilized with an air conditioner for purifying air within a vehicle, and includes a noxious gas sensing apparatus for sensing noxious external air and temperature sensing apparatus for sensing the temperature of the external air.

Traditionally, the noxious gas sensing apparatus and the temperature sensing apparatus are separately disposed on the vehicle, and perform a service thereof.

These separate apparatuses add cost to the system and also increase the system's weight.

The information disclosed in this Background of the Invention section is only for enhancement of understanding of the background of the invention and should not be taken as an acknowledgement or any form of suggestion that this information forms the prior art that is already known in this country to a person of ordinary skill in the art.

SUMMARY OF THE INVENTION

The motivation for the present invention is to provide a sensing apparatus for a vehicle having non-limiting advantages of reduction of size, cost, and weight thereof. An exemplary sensing apparatus for a vehicle according to an embodiment of the present invention includes a case having an opening part formed so as to communicate with an outside. A printed circuit board is disposed inside of the case, and includes a circuit unit. A noxious gas sensing part is electrically connected with the circuit unit for sensing a noxious gas of an external air inflowing through the opening portion, and for outputting a sensing signal. A connector is disposed at least partially within the case, one end thereof being directly connected with the circuit unit, and the other end thereof being directly connected to an external device.

In a further embodiment according to the present invention, the case includes a first member and a second member. A seal member is disposed between the first and second members so as to prevent water from flowing into the case. In another further embodiment according to the present invention, the circuit unit includes a protection circuit for detecting an inverse voltage and a surge that may be inputted into the circuit unit, and stopping an operation of the circuit unit as needed. A unification circuit includes a first function of regulating a voltage supplied from the protection circuit, a second function of supplying the regulated voltage into the circuit unit, and a third function of supplying a heat to the noxious gas sensing part. A signal circuit part generates a control signal on the basis of an outputted signal from the noxious gas sensing part, and transmitting the control signal into an outside device.

In another further embodiment according to the present invention, the unification circuit is integrated as one circuit chip, such that the first, second, and third functions are performed by the one circuit chip.

In another further embodiment according to the present invention, the signal circuit part includes a converter changing the outputted signal from the noxious gas sensing part to a frequency signal. A multifunction circuit provides a first function of calculating a control signal on the basis of the frequency signal, and a second function of matching up the calculated control signal. A driving circuit transmits the matched control signal to an external device.

In another further embodiment according to the present invention, the multifunction circuit further provides a third function of detecting an overvoltage that may be generated while the circuit unit is operated, and stops an operation of the circuit unit based on the detected overvoltage.

In another further embodiment according to the present invention, the multifunction circuit is integrated as one circuit chip, such that the first, second, and third functions are performed by the one circuit chip.

In another further embodiment according to the present invention, the noxious gas sensing part includes a foreign-substance intercepting member disposed on the opening part of the case so as to prevent a foreign-substance from inflowing into the case. A noxious gas sensor is disposed on the one surface of the printed circuit board corresponding to the foreign-substance intercepting member so as to sense a noxious gas of the external air passing through the foreign-substance intercepting member.

In another further embodiment according to the present invention, the noxious gas sensing part further includes a cap having a plurality of openings formed at a surface facing a flow of the external air, and having a guiding passage formed by a lower surface thereof so as to guide an air passing through the openings into the opening part, such that the external air smoothly inflows into the opening part of the case.

In another further embodiment according to the present invention, the foreign-substance intercepting member is a membrane filter for intercepting dust and moisture while allowing passing of external air.

BRIEF DESCRIPTION OF THE DRAWINGS

The accompanying drawings illustrate exemplary embodiments of the present invention, and, together with the description, serve to explain the principles of the present invention, wherein.

DETAILED DESCRIPTION OF THE EMBODIMENTS

An embodiment of the present invention will hereinafter be described in detail with reference to the accompanying drawings.

Figure 1:
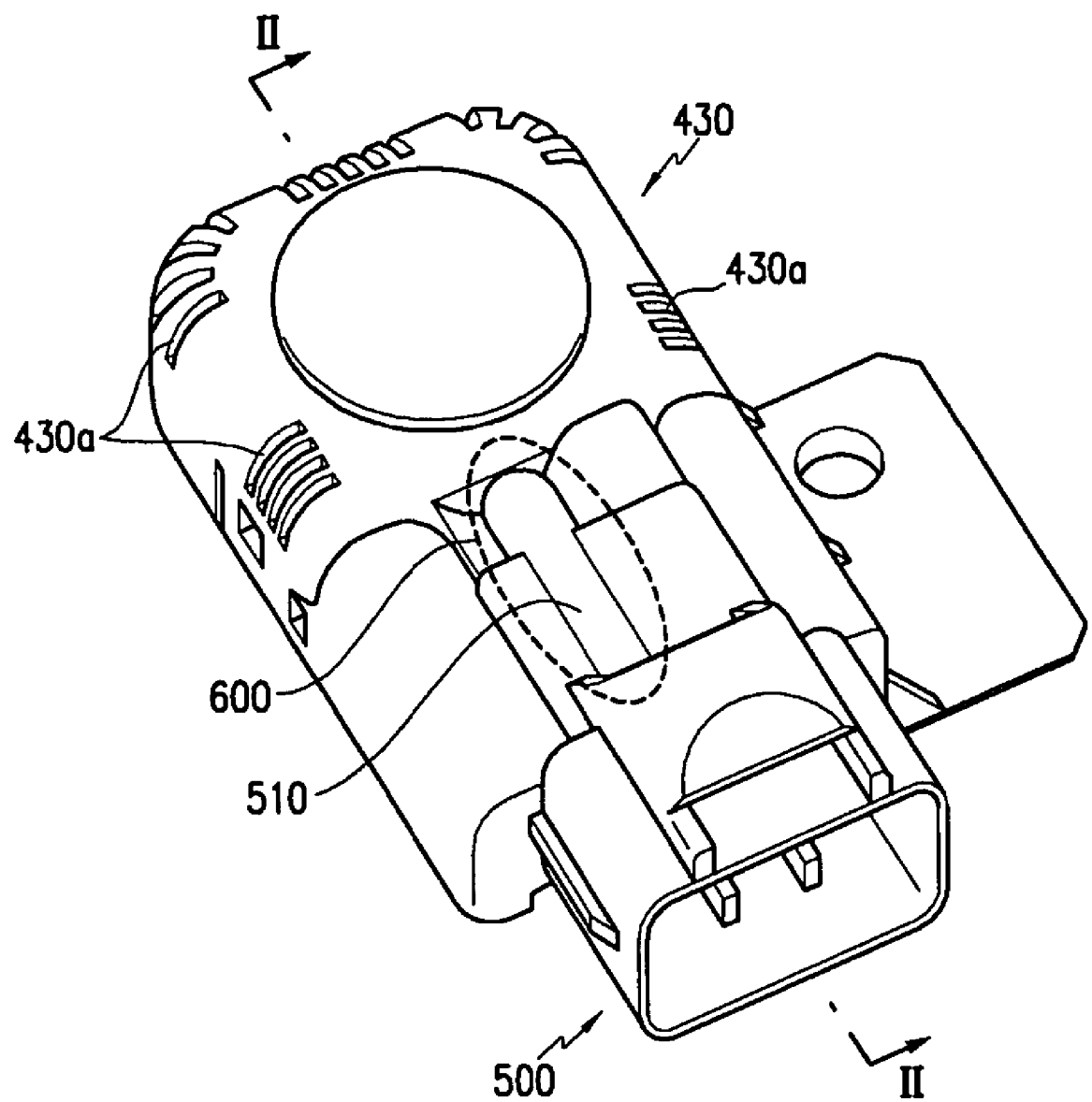
FIG. 1 is a perspective view showing a sensing apparatus for a vehicle according to an embodiment of the present invention.
Figure 2:
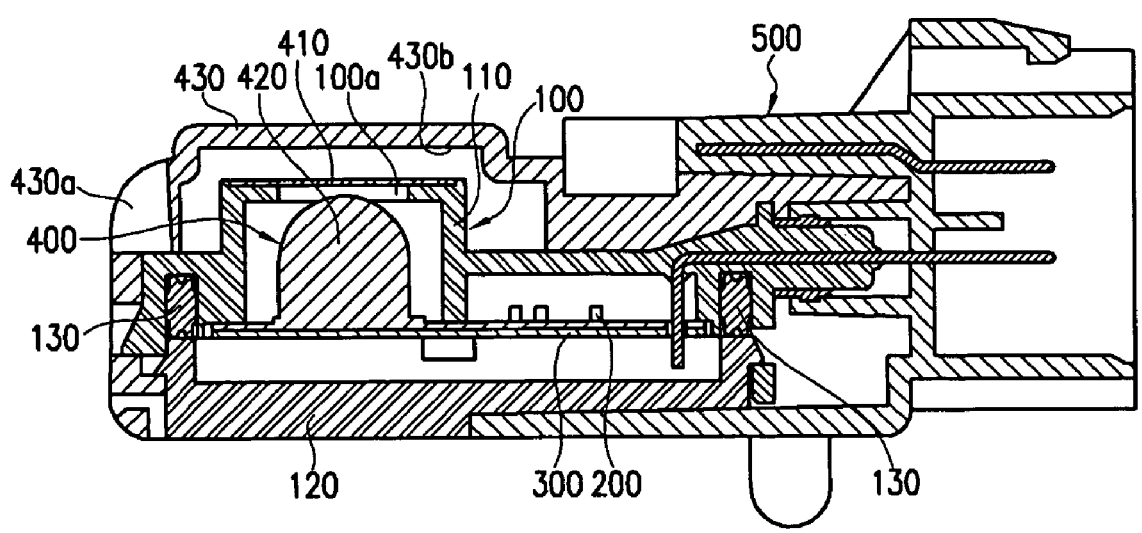
FIG. 2 is a cross-sectional view taken along line II-II in FIG. 1.

FIG. 1 is a perspective view showing a sensing apparatus according to an embodiment of the present invention, and FIG. 2 is a cross-sectional view taken along the line II-II in FIG. 1. As shown, a sensing apparatus for a vehicle includes a case 100, a printed circuit board (PCB) 300, a noxious gas sensing part 400, and a connector 500. The case 100 has an opening portion 100a formed at one portion thereof, such that an inside of the case 100 communicates with the outside. The PCB 300 is disposed inside of the case 100, and includes a circuit unit 200.

The noxious gas sensing part 400 is electrically connected with the circuit unit 200, senses a noxious gas in the external air flowing through the opening portion 100a thereinto, and outputs a sensing signal.

The connector 500 is disposed on another portion of the case 100. One end of the connector 500 is directly connected with the circuit unit 200, and the other end of the connector 500 connects to an outside device (not shown).

As shown in FIG. 2, the case 100 has a structure that is separated into a first member 110 and a second member 120. The first member 110 covers an upper portion of the PCB 300, and the second member 120 covers a lower portion of the PCB 300. Accordingly, the PCB 300 can be easily separated from the case 100 when repair thereof is required.

In addition, the case 100 has a seal member 130 disposed between the first member 110 and the second member 120, so as to prevent water from flowing into the PCB 300. For example, the seal member 130 is inserted into an edge groove of the first member 110.

Particularly, the seal member 130 differs from the conventional epoxy which is fully injected into the case, and therefore, the PCB can not be separated from the case. However, the seal member 130 is only inserted in an edge groove of the first member 110, and therefore, the PCB 300 can be easily separately from the case 100.

In addition, a sensing apparatus according to an embodiment of the present invention can reduce costs and weight in comparison with conventional sensing apparatuses, since the seal member 130 is inserted in only the edge groove of the first member 110.

Figure 3:
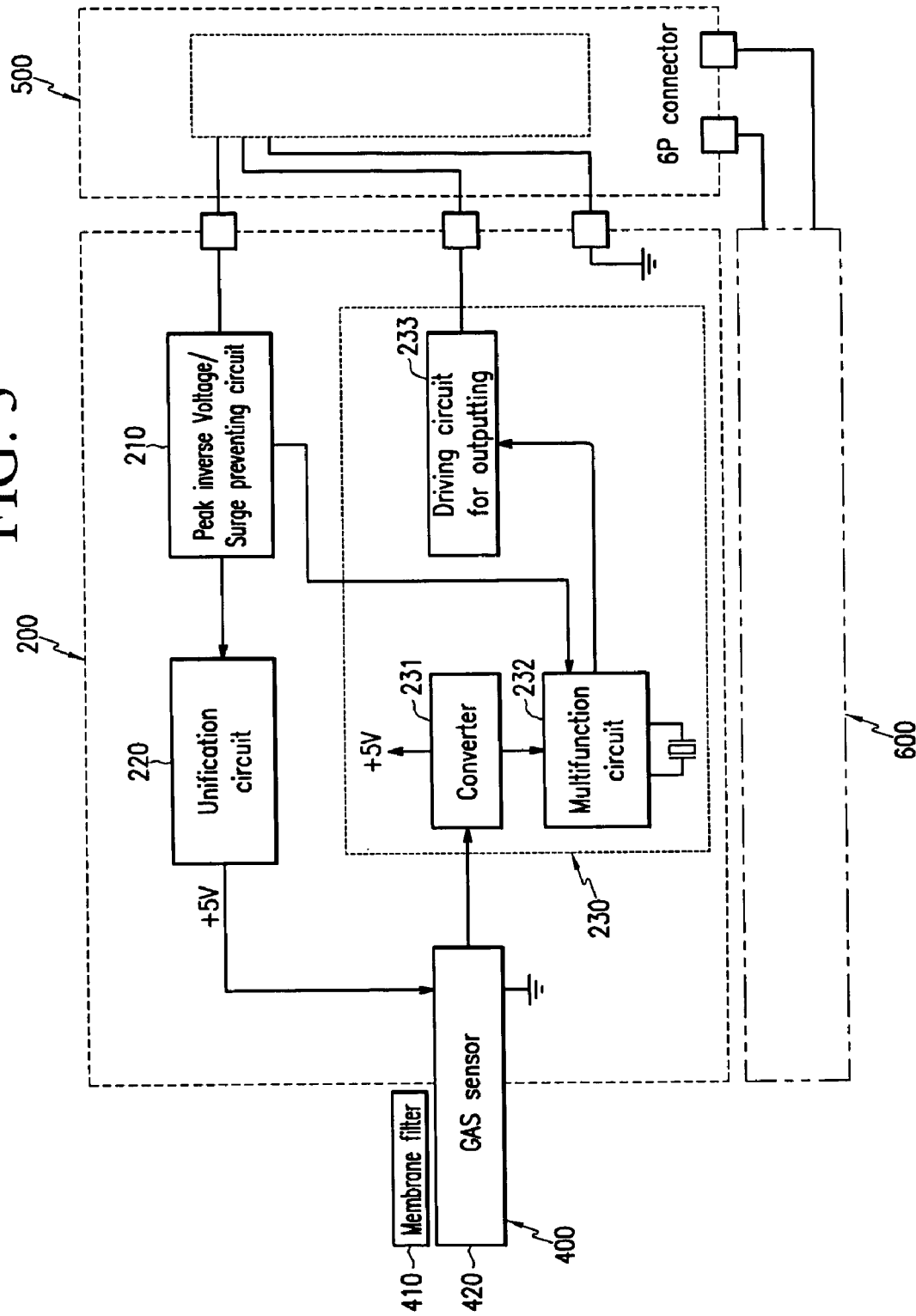
FIG. 3 is circuit diagram showing a circuit unit of a sensing apparatus for a vehicle according to an embodiment of the present invention.

FIG. 3 is a circuit diagram showing a circuit unit of a sensing apparatus for a vehicle according to an embodiment of the present invention. As shown, the circuit unit 200 includes a peak inverse voltage /surge preventing circuit 210, a unification circuit 220, and a signal circuit part 230. The peak inverse voltage/surge preventing circuit 210 detects an inverse voltage and a surge that is inputted into the circuit unit 200, and stops operation of the circuit unit 200 based on the detected inverse voltage and surge.

The unification circuit 220 has a first function of regulating a voltage supplied from the peak inverse voltage/surge preventing circuit 210, a second function of supplying the regulated voltage into the circuit unit 60, and a third function of supplying a heat to the noxious gas sensing part 400. Particularly, so that such functions can be performed together by only one circuit chip, it is preferable that the unification circuit 220 is integrated as one circuit chip.

Accordingly, the size of the circuit unit 200 can be reduced since a conventional driving circuit and a conventional heat producing circuit are together integrated as only one circuit chip. In addition, a size of the PCB can be reduced since the size of the circuit unit 200 can be reduced. Consequently, a size of the case 100 can be reduced, and a cost can be reduced as much as a reduction of the size.

The signal circuit part 230 generates a control signal on the basis of an outputted signal from the noxious gas sensing part 400, and transmits the control signal into an outside device.

As shown in FIG. 3, the signal circuit part 230 includes a converter 231, a multifunction circuit 232, and a driving circuit for outputting 233. The converter 231 changes a signal that is outputted through the noxious gas sensing part 400 to a frequency signal. The multifunction circuit 232 performs a first function of calculating a control signal on the basis of the frequency signal, and a second function of matching up the calculated control signal. Particularly, so that such functions can be performed together by only one circuit chip, it is preferable that the multifunction circuit 232 is integrated as one circuit chip.

Accordingly, a size of the circuit unit 200 can be reduced since a conventional MICOM and a conventional matching circuit are together integrated on only one multifunction circuit 232. In addition, a size of the PCB (see 300 in FIG. 2) can be reduced since the size of the circuit unit 200 can be reduced. Consequently, a size of the case 100 can be reduced, and a cost can be reduced as much as a reduction of the size.

In addition, the multifunction circuit 232 further performs a third function of detecting an overvoltage that may be generated while the circuit unit 200 is operated by the electric power, and stopping an operation of the circuit unit 200 based on the detected overvoltage. Particularly it is more preferable that the multifunction circuit 232 is integrated as one circuit chip, such that the first, second, and third functions are together performed by only one circuit chip.

Accordingly, a sensing apparatus for a vehicle according to an embodiment of the present invention has advantages that a size and a cost can be reduced, since a conventional MICOM, a conventional matching circuit, and a conventional overvoltage detecting circuit are together integrated as only one multifunction circuit 232.

The driving circuit for outputting 233 transmits the matched control signal through the multifunction circuit 232 into an external device (not shown). For example, the driving circuit for outputting 233 may be a driving transistor for outputting.

As shown in FIGS. 1 and 2, the noxious gas sensing part 400 includes a foreign-substance intercepting member 410 and a noxious gas sensor 420. The foreign-substance intercepting member 410 is disposed on the opening part 100a of the case 100, and prevents a foreign-substance from inflowing into inside of the case 100. The noxious gas sensor 420 is disposed on one surface of the PDB 300 corresponding to the foreign-substance intercepting member 410, and senses a noxious gas of the external air passing through the foreign-substance intercepting member 410.

The noxious gas sensing part 400 further includes a cap 430 for smoothly inflowing the external air into the opening part 100a of the case 100. For example, the cap 430 has a plurality of openings 430a formed at a side surface facing a flow of the external air, and has a guiding passage 430b formed by a lower surface thereof so as to guide an air passing through the openings 430a into the opening part 100a.

In addition, the cap 430 also protects the foreign-substance intercepting member 410. In addition, the foreign-substance intercepting member 410 may be a membrane filter. The membrane filter intercepts dust and moisture while allowing passing of external air.

As shown in FIGS. 1 and 3, a sensing apparatus according to an embodiment of the present invention further includes a temperature sensor 600 so as to hold an indoor temperature at a proper temperature. As has been explained above, a sensing apparatus according to an embodiment of the present invention has a number of advantages.

According to the present invention, a PCB can be easily separated from a case when a repair thereof is required, since the first and second members, and the seal member are separately provided.

In addition, according to the present invention, weight and cost can be reduced with comparison to the conventional apparatus, since the seal member is inserted in only the edge groove of the first member.

In addition, according to the present invention, cost, size, and man-hours can also be reduced with comparison to the conventional apparatus, since only one membrane filter is provided so as to intercept a foreign substance.

In addition, according to the present invention, cost, size, and man-hours can also be reduced with comparison to the conventional apparatus, since a conventional lead wire is not required, that is, a connector is directly connected with an outside device.

In addition, according to the present invention, cost, size, and man-hours can also be reduced with comparison to the conventional apparatus, since a unification circuit and a multifunction circuit are respectively integrated as one circuit.

While this invention has been described in connection with what is presently considered to be the most practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A sensing apparatus, comprising:
   a case having an opening part formed so as to communicate within outside of the case;
   a printed circuit board disposed at least partially within the case, and comprising a circuit unit;
   a noxious gas sensing part, being electrically connected with the circuit unit, for sensing noxious gas in external air flowing in through the opening portion, and for outputting a sensing signal; and
   a connector disposed at least partially within the case, one end thereof being directly connected with the circuit unit, and the other end thereof being configured to connect to and external device;
   wherein the circuit unit comprises:
      a protection circuit for detecting an inverse voltage and a surge that may be inputted into the circuit unit, and stopping an operation of the circuit unit as needed;
      a unification circuit having a first function of regulating a voltage supplied from the protection circuit, a second function of supplying the regulated voltage into the circuit unit, and a third function of supplying a heat to the noxious gas sensing part; and
      a signal circuit part generating a control signal on the basis of an outputted signal from the noxious gas sensing part, and transmitting the control signal into an outside device, wherein the signal circuit part comprises:
         a converter changing the outputted signal from the noxious gas sensing part to a frequency signal;
         a multifunction circuit for providing a first function of calculating a control signal on the basis of the frequency signal, a second function of matching to the calculated control signal, and a third function of detecting an overvoltage that may be generated while the circuit unit is operated, and stopping operation of the circuit unit based on the detected overvoltage; and
         a driving circuit for transmitting the matched control signal to the external device.

2. The sensing apparatus of claim 1, wherein the case comprises:
   a first member and a second member; and
   a seal member disposed between the first and second members, so as to prevent water from flowing into the case.

3. The sensing apparatus of claim 1, wherein the unification circuit is integrated as one circuit chip, such that the first, second, and third functions are performed by the one circuit chip.

4. The sensing apparatus of claim 1, wherein the multifunction circuit is integrated as one circuit chip, such that the first, second, and third functions are performed by the one circuit chip.

5. The sensing apparatus of claim 1, wherein the noxious gas sensing part comprises:
   a foreign-substance intercepting member disposed at the opening part of the case so as to prevent a foreign-substance from flowing into the case; and
   a noxious gas sensor disposed on one surface of the printed circuit board corresponding to the foreign-substance intercepting member so as to sense a noxious gas in the external air passing through the foreign-substance intercepting member.

6. The sensing apparatus of claim 5, wherein the noxious gas sensing part further comprises a cap having a plurality of openings formed at a surface facing a flow of the external air, and having a guiding passage formed by a lower surface thereof so as to guide air passing through the openings into the opening part, such that the external air flows into the opening part of the case.

7. The sensing apparatus of claim 5, wherein the foreign-substance intercepting member is a membrane filter for intercepting dust and moisture while allowing passing of external air.

* * * * *